US00RE33965E

United States Patent [19]

Tada et al.

[11] E Patent Number: Re. 33,965

[45] Reissued Date of Patent: Jun. 16, 1992

[54] INTERMEDIATE FOR COMPOSITE MATERIALS

[75] Inventors: Hisashi Tada; Akira Agata; Yasuaki Ii, all of Aichi, Japan

[73] Assignee: Mitsubishi Rayon Co., Ltd., Tokyo, Japan

[21] Appl. No.: 369,496

[22] Filed: Jun. 21, 1989

Related U.S. Patent Documents

Reissue of:

[64] Patent No.: 4,767,805
Issued: Aug. 30, 1988
Appl. No.: 12,236
Filed: Feb. 9, 1987

U.S. Applications:

[63] Continuation-in-part of Ser. No. 763,180, Aug. 7, 1985, abandoned.

[30] Foreign Application Priority Data

Aug. 7, 1984 [JP] Japan ..... 59-164249
Aug. 7, 1984 [JP] Japan ..... 59-164250
Aug. 7, 1984 [JP] Japan ..... 59-164251

[51] Int. Cl.[5] ..... C08K 3/04; C08G 59/64; C08J 5/24

[52] U.S. Cl. ..... 523/468; 523/206; 523/466; 525/423; 528/111

[58] Field of Search ..... 523/468, 206, 466; 528/111; 525/423

[56] References Cited

U.S. PATENT DOCUMENTS 2,994,673 8/1961 Capron et al. ..... 528/111
3,336,253 8/1957 Wong et al. ..... 528/111
4,480,082 10/1984 McLean et al. ..... 528/111

FOREIGN PATENT DOCUMENTS 628159 9/1961 Canada ..... 528/111

OTHER PUBLICATIONS

Derwent Abs 84-295910/48 Gardner et al (EP-126494), Nov. 28, 1984.
Derwent Abs 85-124199/21, Forgo et al (EP-142463), May 22, 1985.
Chem. Abs., 95-63276b (1981), Farberov et al.
Chem. Abs., 88-130822g (1978), Niedzielska et al.

*Primary Examiner*—Herbert J. Lilling
*Attorney, Agent, or Firm*—Sughrue, Mion, Zinn Macpeak & Seas

[57] ABSTRACT

An intermediate for a composite material is disclosed. The intermediate is obtained by impregnating an epoxy resin composition containing a specific additive into a carbon fiber. The composite material obtained from the intermediate has improved mechanical properties.

19 Claims, No Drawings

INTERMEDIATE FOR COMPOSITE MATERIALS

Matter enclosed in heavy brackets [ ] appears in the original patent but forms no part of this reissue specification; matter printed in italics indicates the additions made by reissue.

This is a continuation-in-part of application Ser. No. 763,180, filed Aug. 7, 1985, now abandoned.

FIELD OF THE INVENTION

This invention relates to an intermediate for a composite material having excellent mechanical properties.

BACKGROUND OF THE INVENTION

Various resin compositions have conventionally been used as matrices for composite materials. In the particular field of thermosetting resins, epoxy resins have widely been used as matrix resins because of their excellent mechanical properties, such as strength, elongation, heat resistance, etc., but when reinforcing materials are used composite materials containing reinforcing materials become more or less strengthened and, generally, the strength of reinforcing material is reflected in or transferred to the composite material. However, even in the case of using epoxy resins, the degree of strengthening or transfer due to the reinforcing materials is still unsatisfactory particularly in terms of compression characteristics and, therefore, improvement in this respect has been demanded. An attempt to this effect was directed to an increase in rigidity of resins per se, but generally an increase in rigidity is accompanied with an unfavorable increase in heat resistance, resulting in a significant reduction in elongation. Such resins connot be used in some applications because of their brittleness. It was proposed in *The British Polymer Journal*, 15, 66 (March, 1983) that a reaction product between an epoxy compound

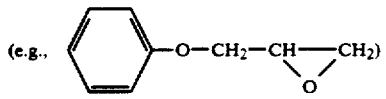

and an amide compound

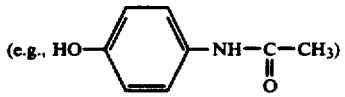

is added to a system comprising an epoxy resin and a hardener to thereby improve the physical properties of resins, but no consideration is given to the improvement of the compression characteristics of the composites when they are used as a matrix resin for composite materials. In connection to the above proposal, there have also been proposed a reaction product between an epoxy compound and an amine compound in EP-A-103392 and a reaction product between an epoxy compound and an amide compound in EP-A-103968, but neither contains any suggestion of these materials for use as a matrix resin for composite materials.

SUMMARY OF THE INVENTION

In the light of these circumstances, the present inventors have conducted extensive studies on intermediate for composite materials which can provide excellent mechanical properties, particularly compression characteristics. As a result, they discovered an additive which can remarkably improve the rigidity of cured epoxy resins without impairing their elongation and confirmed that an epoxy resin composition comprising an epoxy resin, a hardener, a hardening accelerator and the above-described additive when used as a matrix gives pronouncedly improved composite mechanical properties.

The present invention relates to an intermediate for a composite material, which is obtained by impregnating a reinforcing material with an epoxy resin composition containing, as an additive, at least one of compounds represented by the following formulae (I)

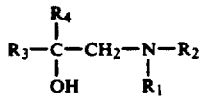

(I)

wherein $R_1$, $R_2$ which may be the same or different, each represents a propyl group, a butyl group, etc), a substituted or unsubstituted, saturated alicyclic group having 5 to 17 carbon atoms (e.g., a cyclopentyl group, a cyclohexyl group, a 2-ethylcyclohexyl group, etc.), a substituted or unsubstituted aromatic group having 6 to 17 carbons atoms (e.g., a phenyl group, a tolyl group, etc.), or a substituted or unsubstituted, saturated or unsaturated 5- or 6-membered heterocyclic group containing N, O or S as hetero atom

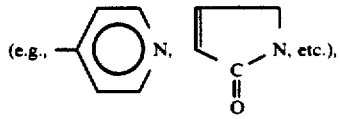

or a group of formula

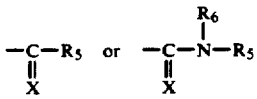

wherein $R_5$ and $R_6$, which may be the same or different, each represents a hydrogen atom or a substituted or unsubstituted, saturated aliphatic group having 1 to 17 carbon atoms (e.g., a methyl group, an ethyl group, an ethyl hexyl group, etc.), a substituted or unsubstituted, saturated alicyclic group having 5 to 17 carbon atoms (e.g., a cyclopentyl group, a cyclohexyl group, a 2-ethylhexyl group, etc.), a substituted or unsubstituted aromatic group having 6 to 17 carbon atoms (e.g., a phenyl group, a tolyl group, etc.), or a substituted or unsubstituted, saturated or unsaturated 5- or 6-membered heterocyclic group containing N, O or S as hetero atom

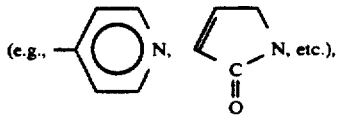

wherein said substituted aliphatic, alicyclic, aromatic and heterocyclic groups may contain as a substituent a halogen atom (e.g., chlorine, bromine, etc.), an alkoxy group having 1 to 3 carbon atoms (e.g., a glycidyloxy group, a methoxy group, an ethoxy group, etc.), an aryloxy group having 6 to 17 carbon atoms (e.g., a phenoxy group, etc.), an acyl group having 2 to 7 carbon atoms (e.g., an acetyl group, a benzoyl group, etc.); $R_3$ and $R_4$, which may be the same or different, each has the same meanings as defined for $R_1$ and $R_2$, or a group of formula R—$OCH_2$— wherein R has the same meaning as defined for $R_1$ and $R_2$

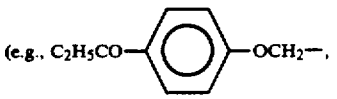

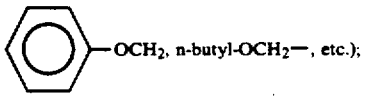

and X represents an oxygen atom, a sulfur atom or N—$R_7$ wherein $R_7$ represents a hydrogen atom or has the same meaning as defined for $R_1$ and $R_2$.

DETAILED DESCRIPTION OF THE INVENTION

Among the compounds represented by the formulae (I), this having a bulky and highly rigid substituent, such as an aromatic group, a heterocyclic group and an alicyclic group, in the molecule thereof are particularly effective.

Specific examples of the compounds which can preferably be used in the present invention are shown below:

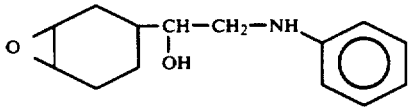

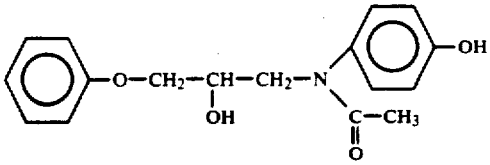

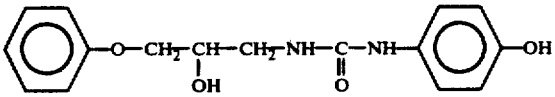

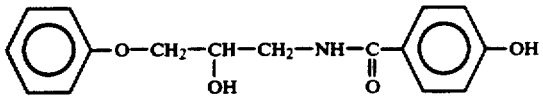

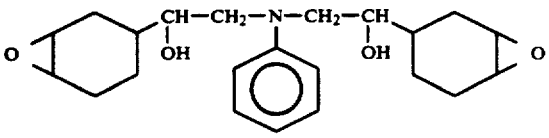

-continued

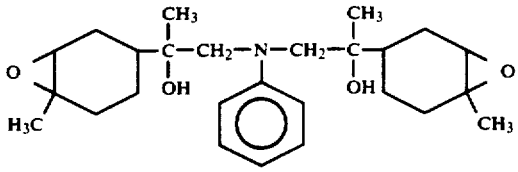

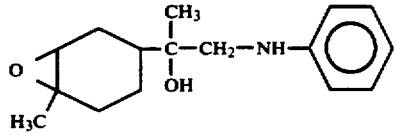

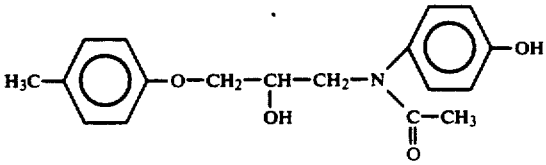

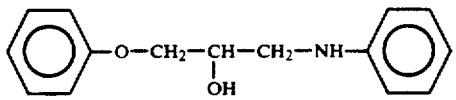

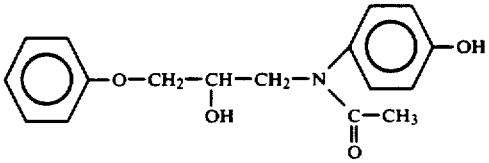

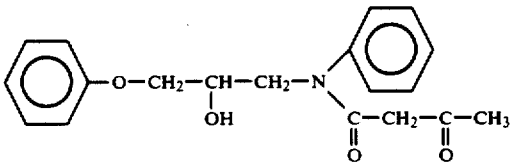

[

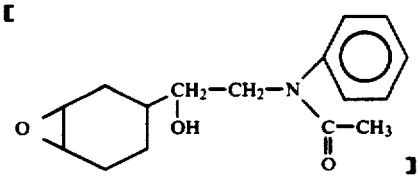

]

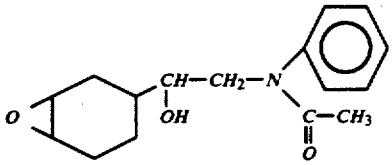

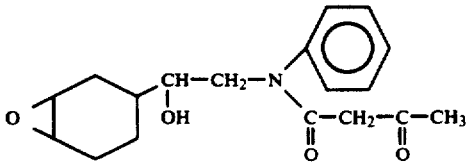

-continued
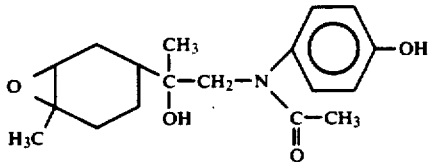
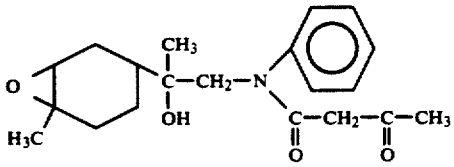
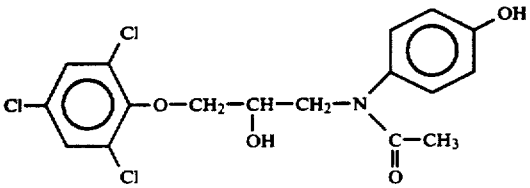
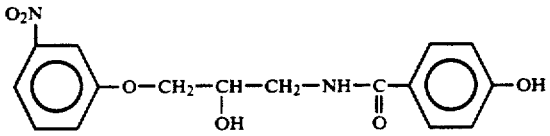
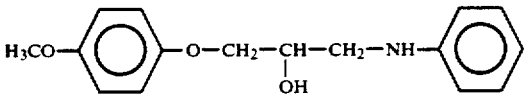
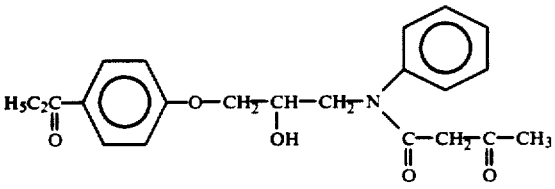
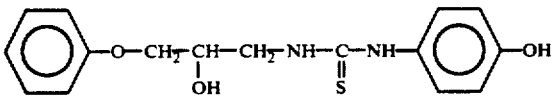
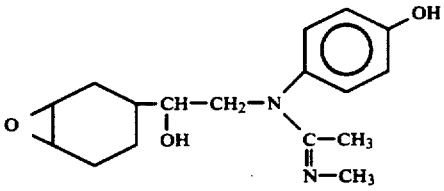
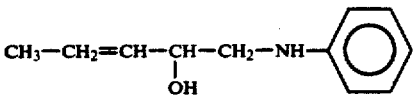
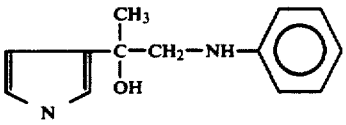
-continued
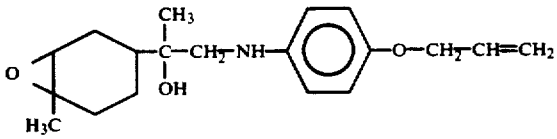
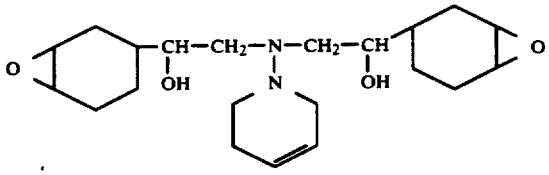
Of these, more preferred are the following compounds.
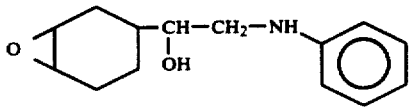
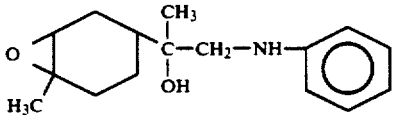
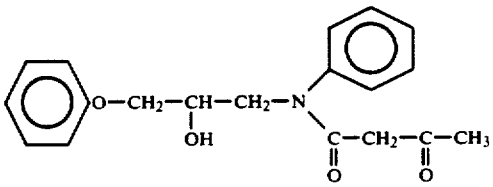
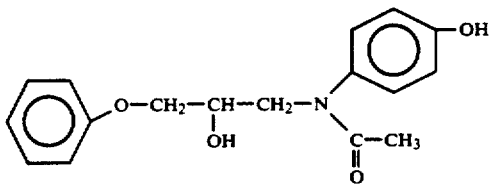
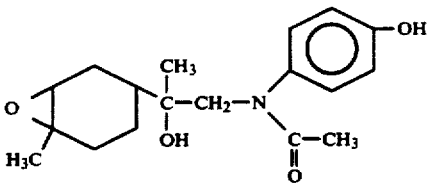
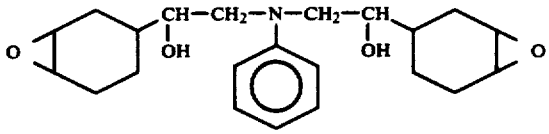
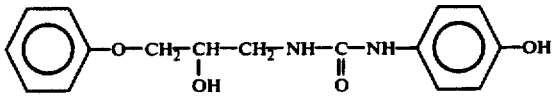

-continued

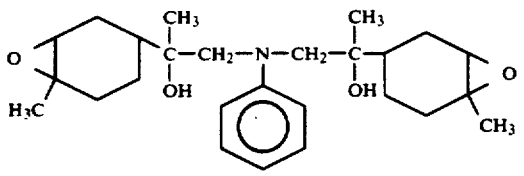

The compounds represented by the formula (I) can be obtained, for example, through reactions between epoxy compounds and the corresponding amine compounds, amide compounds and urea compounds, respectively, as shown in the following reaction schemes:

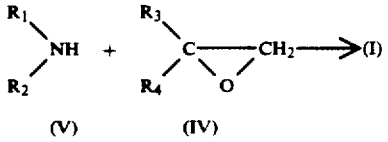

(V) (IV)

wherein $R_1$ to $R_4$ and X are as defined above.

The epoxy compounds represented by the formula (IV) which can be used in the preparation of the compounds of the present invention include low molecular epoxy compounds, such as epichlorohydrin, phenylglycidyl ether, ethylene oxide, propylene oxide, butadiene oxide, dimethylpentane dioxide, diglycidyl ether, butanediol diglycidyl ether, ethylene glycol diglycidyl ether, vinylcyclohexene dioxide, limonene dioxide, bis(2,3-epoxycyclopentene) ether, divinylbenzene dioxide, resorcin diglycidyl ether, 2-glycidyl phenylglycidyl ether, 3,4-epoxy-6-methyl-cyclohexylmethyl-3,4-epoxymethylcyclohexenecarboxylate, butylglycidyl ether, styrene oxide, p-butylphenol glycidyl ether, cresylglycidyl ether, glycidyl methacrylate, allylglycidyl ether, cyclohexanevinyl monoxide, dipentene monoxide, α-pinene oxide, 3(pentadecyl) phenylglycidyl ether, etc.

The compounds represented by the formula (V) which can be used in the above-described reaction (A) include alicyclic amines, e.g., cyclohexylamine, dicyclohexylamine, etc.; aromatic amines, e.g., aniline, p-aminobenzoic acid, 3,4-xylidine, m-xylylenediamine, diaminodiphenyl ether, dibenzylamine, benzylamine, etc.; heterocyclic amines, e.g., 4-aminopyridine, N-aminopropylmorpholine, bisaminopropylpiperazine, etc., heterocyclic compounds, e.g., piperazine, 2-pipecoline, piperidine, pyrrolidine, 5-fluorouracil, N-methylpiperazine, etc.; and amino acids, e.g., β-alanine, glycylglycine, glutamic acid, γ-aminobutyric acid, γ-aminocaproic acid, glycine, etc.; acid amides, e.g., 4-hydroxyphenylamide, 4-hydroxyphenylacetamide, phenylacetoacetamide, etc., or corresponding monothio- or dithiocarboxylic acids thereof; acetoguanamine; 3-amino-1, 2,4-triazole isocyanuric acid; imidiazoles, e.g., 2-methylimidazole, 2-ethyl-4-methylimidazole, 2-phenylimidazole, 2-undecylimidazole, 2-heptadecylimidazole, 2,4-diamino-6-[2'-methylimidazolyl-(1)']-ethyl-s-triazine, 2,4-diamino-6-[2'-ethyl-4-methylimidazolyl-(1)']-ethyl-s-triazine, 2-phenyl-4-methyl-5-hydroxymethylimidazole, 2-phenyl-4,5-dihydroxymethylimidazole, a 2-methylimidazole-isocyanuric acid adduct, a 2-phenylimidazole-isocyanuric acid adduct, etc.; 5,5-dimethylhydantoin; benzoguanamine; 1-methylol-5,5-dimethylhydantoin, melamine; 1,3-diphenylguanidine; di-o-tolylguanidine; 1-o-tolylbiguanide, and the like; single or mixed asymmetrical urea or thiourea compounds derived from ammonia; aliphatic amines, e.g., methylamine, ethylamine, n-propylamine, n-butylamine, isopropylamine, 2-ethylhexyloxypropylamine, 3-ethoxypropylamine, di-2-ethylhexylamine, dibutylaminopropylamine, diisobutylamine, 3-methoxypropylamine, allylamine, secbutylamine, isopropanolamine, 2-ethylhexylamine, ethylenediamine, hexamethylenediamine, etc.; alicyclic amines, e.g., cyclohexylamine, dicyclohexylamine, etc.; aromatic amines, e.g., aniline, p-aminobenzoic acid, 3,4-xylidine, dibenzylamine, benzylamine, etc.; heterocyclic amines, e.g., 4-aminopyridine, N-aminopropylmorpholine, 1-amino-1-methylpiperazine, bisaminopropylpiperazine, etc., heterocyclic compounds, e.g., piperazine, 2-pipercoline, piperidine, pyrrolidine, 5-fluorouracil, morpholine, N-methylpiperazine, etc.; and amino acids, e.g., β-alanine, glycylglycine, glutamic acid, γ-aminobutyric acid, γ-aminocaproic acid, glycine, etc.; acetoguanamine, 3-amino-1,2,4-triazole, osocyanuric acid, imidazoles, e.g., 2,4-diamino-6-[2'-methylimidazolyl-(1)']ethyl-s-triazine, 2,4-diamino-6-[2'-undecylimidazolyl-(1)']ethyl-s-triazine, 2,4-diamino-6-[2'-ethyl-4'-methylimidazolyl-(1)']-ethyl-s-triazine, a 2-methylimidazole-isocyanuric acid adduct, a 2-phenylimidazole-isocyanuric acid adduct. etc., 5,5-dimethylhydantoin, benzoguanamine, 1-methylol-5,5-dimethylhydantoin, melamine, 1,3-diphenylguanidine, di-o-tolylguanidine, 1-o-tolybiguanide, N,N'-diphenylthiourea, 2-mercapto-2-imidazoline, N,N'-diethylthiourea, N,N'-dibutylthiourea, N,N'-diluarylkthiourea, and the like.

The reaction (A) can be carried out in the presence or absence of an organic solvent at a temperature of from room temperature to 180° C. while stirring for 0.5 to 10 hours. The solvent to be used include aromatic hydrocarbons, e.g., benzene, toluene, etc.; aliphatic hydrocarbons, e.g., hexane, ligroin, etc.; halogenated hydrocarbons, e.g., carbon tetrachloride, chloroform, etc.; and ethers, e.g., dioxane, tetrahydrofuran, etc. In carrying out the reaction the chemical equivalent ratio of epoxy group to an NH bond ranges from 1/10 to 10/1, and preferably from 1/1.5 to 1.5/1. (cf. Henry Lee and Kris Neville; Handbook of Expoxy Resins", S.5-12 and 5-13 McGraw-Hill Book Co., 1967))

SYNTHESIS EXAMPLE 1

Synthesis of Compound B-3

In a flask equipped with a condenser, a dropping funnel and a stirrer, there was placed 168 g of vinylcyclohexene dioxide and heated at 170° C. while stirring. Aniline (93 g) contained in the dropping funnel was added portionwise at a rate of 2 g/min. After completion of addition, the mixture was allowed to react for 1 hour to obtain a composition. Formation of Compound B-3 was confirmed by NMR spectral analysis.

SYNTHESIS EXAMPLE 2

Synthesis of Compound B-7

4-Hydroxyphenylacetamide (150 g) was dissolved in 160 g of phenyl glycidyl ether and the solution was stirred for 5 hours at 90° C. to obtain a viscous liquid composition. Formation of Compound B-7 was confirmed by NMR spectral analysis.

The epoxy resin composition for intermediate for composite materials according to the present invention usually comprises from 2 to 150 parts by weight, and preferably from 10 to 50 parts by weight, of the above-described additive per 100 parts by weight of the total amount of the resin composition (an epoxy resin, a hardener and/or a hardening accelerator). If the amount of the additive is less than 2 parts by weight, a substantial effect cannot be exerted. Amounts exceeding 150 parts by weight seriously reduce heat-resistance.

The epoxy resin to be used in the epoxy resin composition includes well-known epoxy resins, such as polyglycidyl ethers of diphenylolalkanes, e.g., diphenylolpropane, diphenylolethane, diphenylolmethane, etc.; polyhydric phenol polyglycidyl ethers, e.g., novolak, resol, etc.; epoxy resins produced by epoxidation of alicyclic compounds (e.g., cyclohexane, cyclopentadiene, dicyclopentadiene, (etc.), e.g., an ester of 3,4-epoxy-6-methylcyclohexanecarboxylic acid and methyl 3,4-epoxy-6-methylcyclohexanoate; poly(epoxyalkyl) ethers of aliphatic polyoxy compounds, e.g., ethylene glycol, glycerin, etc.; epoxyalkyl esters of carboxylic acids, e.g., glycidyl esters of aromatic or aliphatic carboxylic acids; and the like. These epoxy resins may be used alone or in combination thereof.

A preliminary condensate between the above-enumerated epoxy resin and a hardener may also be employed as epoxy resin of the epoxy resin composition.

The preliminary condensate which can be used in the present invention can be prepared by subjecting at least one polyamine or acidic substance having a polycarboxylic group, a polycarboxylic acid anhydride group or a mixed group thereof and the above-mentioned epoxy resin to heat treatment to increase the viscosity of the mixture at least 3 times without inducing gelation.

Examples of the polyamine to be used for obtaining the preliminary condensate are aromatic polyamines, e.g., o-phenylenediamine, m-phenylenediamine, 4,4'-methylenedianiline, 4,4'-diaminodiphenylsulfone, 3,3'-diaminodiphenylsulfone, m-xylylenediamine, etc.; and aliphatic polyamines, e.g., triethylenetetramine, diethylenetriamine, isophoronediamine, 1,3-diaminocyclohexane, menthanediamine, cyanoethylated diethylenetriamine, N-aminoethylpiperazine, methyliminobispropylamine, aminoethylethanolamine, polyethylenediamine, polymethylenediamine, etc. These polyamines can be used alone or in combination thereof.

Examples of the acidic substance which can be used as a hardener for obtaining the preliminary condensate are phthalic anhydride, succinic anhydride, maleic anhydride, hexahydrophthalic anhydride, pyromellitic anhydride, benzophenonetetracarboxylic anhydride, trimellitic anhydride, itaconic anhydride, citraconic anhydride, dodecenylsuccinic anhydride, chlorendic anhydride, methylcyclopentadiene-maleic acid adduct, methyltetrahydrophthalic anhydride, maleic anhydride-linoleic acid adduct, cyclopentanetetracarboxylic anhydride, alkylated endalkylenetetrahydrophthalic anhydrides, ethylene glycol bistrimellitate, glycerin tristrimellitate, and the like. These acidic substances may be used alone or in combination of two or more thereof.

The chemical equivalent ratio of the polyamine or acidic substance to the epoxy resin is important and ranges from 1:1 to 1:6, preferably from 1:1.4 to 1:6, and more preferably from 1:1.5 to 1:5. If this equivalent ratio is more than 1:1, the excess polyamine or acidic substance reduces heat resistance, strength and the like of a hardened product. On the other hand, if it is less than 1:6 the polyamine or acidic substance becomes short to deteriorate heat resistance or strength of a hardened product. The term "chemical equivalent ratio" as herein used means that one epoxy group is equivalent to one N—H bond or carboxylic acid group or one half carboxylic acid anhydride group.

The temperature for the heat treatment for obtaining the preliminary condensate is determined depending on the time required for reaching a desired viscosity and controllability of viscosity. When the epoxy resin is used in a large excess within the above-described range, it is possible to shorten the treating time by raising the heating temperature. On the other hand, when the epoxy resin is used in a slight excess, the reaction mixture is readily gelled so that the heating temperature should be controlled lower. In general, the heating temperature ranges from 50° to 200° C., and preferably from 120° to 170° C.

The condensation reaction is usually carried out under normal pressure, but may be effected under pressure. The reaction is usually conducted in the absence of a solvent, but when any one or more of the epoxy resins, polyamines and acidic substances are solid at room temperature, solvent may be employed. Such being the case, hydrocarbons that do not adversely affect the produced preliminary condensate, such as xylene, toluene, cyclohexane, etc., are preferred. In the case where a solvent is employed, the resulting reaction mixture containing the solvent may be used as such depending upon the application of the product. If necessary, the solvent may be removed from the reaction mixture by distillation under reduced pressure or a like technique.

The reaction is stopped at the point when the viscosity of the reaction mixture is increased to at least three times the initial one. The upper limit of the viscosity is not particularly restricted as long as gelation does not occur, but the reached viscosity is usually from 10 to 100 times the initial one. The term "viscosity" as herein used means a viscosity as determined by a Brookfield viscometer. The stopping of the reaction can be effected by a known method appropriately selected according to the purpose, for example, a method of quenching the reaction mixture to room temperature, a method of adding a solvent inert to an epoxy group, e.g., acetone, methyl ethyl ketone, toluene, xylene, etc., a method of spreading the reaction mixture in thin film over a cooled plate, and the like.

Use of the above-described preliminary condensate in the epoxy resin composition of the present invention has the following advantages. Those prepared from polyamines and epoxy resins improve working stability (working life) of the composition and also alleviate toxicity and moisture-absorbing property of polyamines as compared with a mere blend of the polyamines (hardener) and epoxy resins. Those prepared from the acidic substances and epoxy resins achieve reduction in a hardening temperature and a hardening time as compared with a mere blend of the acidic substances (hardener) and epoxy resins. Further, these preliminary condensates also have an advantage of possible reduction of a rate of contraction upon hardening.

The hardener which can be added to the epoxy resin composition according to the present invention includes polyamines, such as those enumerated above with respect to the preliminary condensates; acidic substances, such as those enumerated above with respect to the preliminary condensates; and, in addition, acid hydrazides, such as isophthalic acid hydrazide, adipic acid hydrazide, sebacic acid hydrazide, etc.; polyamideamines; dicyandiamide; 1-o-tolylbiguanide; ketimine; and the like. Of these, dicyandiamide is particularly preferred in view of sufficient preservability and working stability of the resulting epoxy resin composition.

The hardening accelerator which can be added to the epoxy resin composition in accordance with the present invention include boron trifluoride complexes, e.g., a boron trifluoride monoethylamine complex compound, a boron trifluoride piperidine complex compound, etc.; imidazole compounds, e.g., 2-methylimidazole, 2-ethyl-4-methylimidazole, etc.; triphenyl phosphite; butanetetracarboxylic acid; 1,8-diazabicyclo(5.4.0)undecene-7; and urea compounds represented by the formula (VIII):

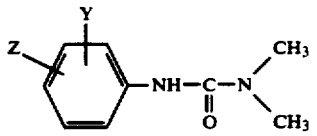

(VIII)

wherein Y and Z, which may be the same or different, each represents a hydrogen atom, a chlorine atom, a bromine atom, a nitro group, a methyl group, a methoxy group or an ethoxy group.

Of the above-mentioned hardening accelerator, the urea compounds represented by the formula (VIII) are particularly preferred since the epoxy resin composition containing the same has sufficient preservability and is rapidly hardenable at relatively low temperatures. Specific examples of the urea compounds of the formula (VIII) are N-(3-chloro-4-methoxyphenyl)-N',N'-dimethylurea, N-(4-chlorophenyl)-N',N'-dimethylurea, N-(3-chloro-4-ethylphenyl)-N',N'-dimethylurea, N-(3-chloro-4-methylphenyl-N',N'-dimethylurea, N-(3,4-dichlorophenyl)-N',N'-dimethylurea, N(4-ethoxyphenyl)-N',N'-dimethylurea, N-(4-methyl-3-nitrophenyl-N',N'-dimethylurea, and the like.

The epoxy resin composition according to the present invention essentially comprises the aforesaid epoxy resin and hardener at the so-called chemical equivalent ratio. If in using the hardening accelerator, the hardener is desirably added in an amount lower than the chemical equivalent ratio. More specifically, the hardener is used in amounts of 40 to 90%, preferably 50 to 80%, of the chemical equivalent amounts based on the total epoxy functional group. If the amounts of hardener is less than 40% of the chemical equivalent amounts, heat resistance of the hardened product is insufficient, and if it exceeds 90% of the chemical equivalent amounts, the hardened product becomes brittle.

The hardening accelerator is used in amounts of from 1 to 15 parts by weight per 100 parts by weight of the total amount of the epoxy resin and the additive. If the amount of the hardening accelerator is less than 1.5 parts by weight, reduction of the hardening temperature cannot be achieved, and amounts exceeding 15 parts by weight decreases the molecular weight to deteriorate heat resistance. Moreover, when the additives of the formula (I) according to the present invention contain a functional group which contributes to hardening, it is desirable to decrease the amount of the hardener depending on the functionality of such a functional group.

Reinforcing materials in which the epoxy resin composition is impregnated to prepare an intermediate material for a composite include chops, yarns, tapes, sheets, knitted products, mats and paper-like products made of carbon fiber.

Impregnation of the epoxy resin composition of the present invention into carbon fiber can be carried out by a hot-melt method or a lacquer method, either directly or after film formation. Direct impregnation by a lacquer method is easier.

The intermediate material, the so-called prepreg, thus obtained can be molded under appropriate conditions of pressure, temperature and time to provide composites having extremely excellent mechanical strength.

The present invention will now be illustrated in greater detail with reference to examples and comparative examples which are given for illustrative purposes only but not for limitation.

EXAMPLES 1 to 9 AND COMPARATIVE EXAMPLES 1 TO 3

In a heating apparatus equipped with a stirrer were placed 100 g of an epoxy resin ("Epikote 828", a trade mark for a product manufactured by Shell Chemicals Corp.) and 9 g of 4,4'-diaminodiphenylsulfone, and the mixture was polymerized at 150° C. for 4 hours while stirring. The reaction mixture was spouted in thin film over an ice-cooled panel to stop the polymerization to obtain Preliminary Condensate (A-1).

Additive (B) (the kind and amount are shown in Table 1 below) and 3 g of N-(3,4-dichlorophenyl)-N',N'-dimethylurea were added to 100 g of Preliminary Condensate (A-1), and the mixture was mixed with stirring at 50° C. to obtain Resin Composition (C). Resin Composition (C) thus obtained was pasty immediately after the preparation and turned out to be an insoluble and non-melting, transparent solid in 30 minutes at 130° C.

The pasty composition had a working life of 1 month or longer at 25° C. as determined by allowing a 50 g portion of the composition before hardening to stand at room temperature and measuring the time at which the viscosity sharply increased.

Then, Resin Composition (C) was cell-casted and hardened at 130° C. for 60 minutes to form a resin plate. The resulting resin plate was subjected to bending test to obtain bending strength, modulus of elasticity in blending and elongation, and the results obtained are shown in Table 1 below. The bending test was carried out under the condition of L/D=16 using a sample piece of 1'×4×60 mm.

Further, 60 g of the pastry resin composition was dissolved in 40 g of methyl ethyl ketone to form a uniform solution. The resulting resinous solution was impregnated into carbon fibers ("Pilofil T-1", a trade mark for a product manufactured by Mitsubishi Rayon Company Limited), and the carbon fiber having impregnated therein the resin solution was wound around a drum, which had previously been covered with a release paper coated with silicone, at a given width. The release paper was taken off from the drum and the resin-impregnated carbon fiber was dried at 70 ° C. for 15 minutes to prepare a prepreg having a resin content of 40% by weight. The resulting prepreg had a gelation time of 45 minutes or more at 140° C. as determined in accordance with JIS K-5909 and a working life of 1 month or more at 25° C.

The prepregs thus produced were laminated in one direction and hardened at 130° C. for 60 minutes, and the hardened product was subjected to heat distortion temperature test and bending test. The heat distortion temperature was determined under a load of 264 psi in parallel to the fiber axis direction in accordance with ASTM D648, and the bending test was conducted under the condition of L/D=40 using a sample piece of 2'×10×100 mm. The heat distortion temperature was 150° C. or higher in each case, and the results of the bending test are shown in Table 1 below.

In Table 1, the following compounds were used as Additive B.

-continued

Additive B

B-7

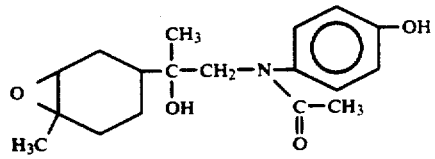

TABLE I

| Run | Additive Kind | Additive Amount (g) | Properties of Resin Plate: Bending Strength (Kg/mm²) | Properties of Resin Plate: Modulus of Elasticity in Bending (Kg/mm²) | Properties of Resin Plate: Elongation (%) | Properties of Composite: Bending Strength (Kg/mm²) | Properties of Composite: Modulus of Elasticity in Bending (Kg/mm²) | Properties of Composite: Elongation (%) |
|---|---|---|---|---|---|---|---|---|
| Example 1 | B-1 | 30 | 21 | 565 | 8.8 | 215 | $13.3 \times 10^3$ | 1.5 |
| Example 2 | B-2 | 5 | 22 | 572 | 8.9 | 216 | $13.4 \times 10^3$ | 1.6 |
| Example 3 | B-2 | 30 | 25 | 590 | 9.2 | 229 | $13.6 \times 10^3$ | 1.8 |
| Example 4 | B-2 | 70 | 21 | 573 | 9.7 | 214 | $13.5 \times 10^3$ | 1.7 |
| Example 5 | B-3 | 30 | 23 | 585 | 9.0 | 227 | $13.4 \times 10^3$ | 1.8 |
| Example 6 | B-4 | 20 | 22 | 574 | 8.9 | 220 | $13.2 \times 10^3$ | 1.6 |
| Example 7 | B-5 | 30 | 21 | 569 | 8.6 | 217 | $13.2 \times 10^3$ | 1.6 |
| Example 8 | B-6 | 40 | 24 | 592 | 9.1 | 230 | $13.5 \times 10^3$ | 1.7 |
| Example 9 | B-7 | 10 | 22 | 571 | 8.7 | 218 | $13.3 \times 10^3$ | 1.6 |
| Comparative Example 1 | — | — | 18 | 367 | 5.5 | 181 | $12.4 \times 10^3$ | 1.4 |
| Comparative Example 2 | B-3 | 0.5 | 18 | 381 | 5.7 | 184 | $12.5 \times 10^3$ | 1.5 |
| Comparative Example 3 | B-3 | 170 | 17 | 310 | 10.4 | 165 | $12.3 \times 10^3$ | 1.5 |

Additive B

B-1

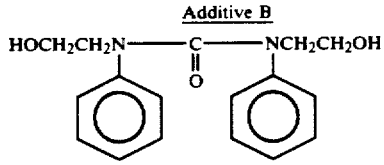

B-2

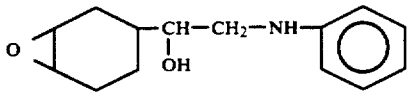

B-3

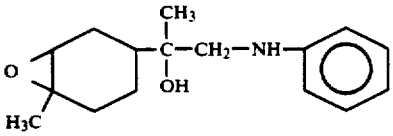

B-4

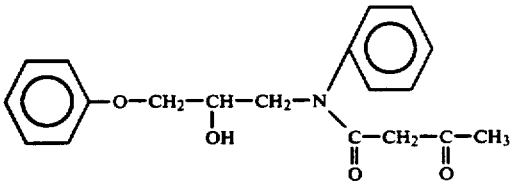

B-5

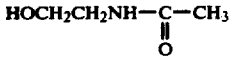

B-6

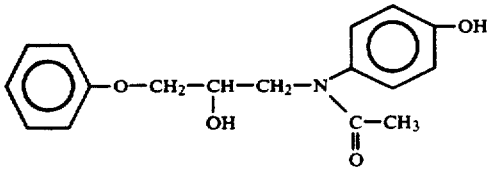

EXAMPLES 10 TO 14 AND COMPARATIVE EXAMPLES 4 TO 6

In a heating apparatus equipped with a stirrer were charged 100 g of Epikote 818 and Additive B as shown in Table 2 below, and the mixture was uniformly mixed at 60° C. for 10 minutes with stirring. A hardener and a hardening accelerator as shown in Table 2 were added thereto, followed by uniformly mixing at 60° C. for 10 minutes to obtain Resin Composition (E).

Resin Composition (E) was molded into a plate at 130° C. for 60 minutes by a cell-casting method, and the resulting molded product was subjected to bending test in the same manner as in Example 1. The results obtained are shown in Table 2 below.

Further, Resin Composition (E) was uniformly impregnated into carbon fibers, and the resin-impregnated carbon fibers were orientated in one direction to form a sheet prepreg. The prepregs thus obtained were laminated and hardened in a mold at 90 ° C. for 1 hour and then at 130° C. for 1 hour under a pressure of 7 Kg/cm². The hardened product was subjected to bending test in the same manner as in the foregoing examples, and the results obtained are shown in Table 2 below.

In Table 2, the following compounds were used as Additive B, hardener and hardening accelerator.

Additive B

B-8

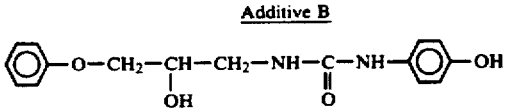

-continued

B-9

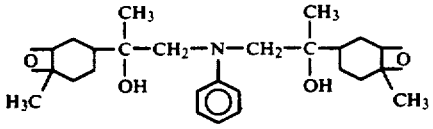

| | |
|---|---|
| | Hardener |
| H-1 | 4,4'-Methylenedianiline |
| H-2 | Dicyandiamide |
| | Hardening Accelerator |
| HA-1 | N-(3,4-Dichlorophenyl)-N',N'-dimethylurea |
| HA-2 | N-(3-Chloro-4-methylphenyl)-N',N'-dimethylurea |
| HA-3 | N-(4-Chlorophenyl)-N',N'-dimethylurea |
| HA-4 | N-(2-Chlorophenyl)-N',N'-dimethylurea |
| HA-5 | N-(4-Ethoxyphenyl)-N',N'-dimethylurea |

TABLE 3-continued

| | | | | |
|---|---|---|---|---|
| | formamide | | Glycol Diglycidyl Ether | |
| B-15 | 4-Hydroxy-acetanilide | 151 | Vinylcyclo-hexene Dioxide | 140 |
| B-16 | Acetanilide | 135 | Phenyl Glycidyl Ether | 150 |
| B-17 | N,N-Dimethylurea | 88 | Epichloro-hydrin | 56.5 |
| B-18 | N,N'-Diallylurea | 140 | Dimethyl-pentane Dioxide | 168 |
| B-19 | N,N'-Di-n-butylurea | 172 | Butadiene Oxide | 70 |
| B-20 | N,N'-Dibenzylurea | 240 | Divinyl-benzene Dioxide | 162 |
| B-21 | Acetanilide | 177 | Vinylcyclo-hexene Dioxide | 140 |
| B-22 | N,N'-Diethyl-thiourea | 120 | Limonene Dioxide | 168 |

TABLE 2

| | Additive | | Hardener | | Hardening Accelerator | | Properties of Resin Plate | | | Properties of Composite | | |
|---|---|---|---|---|---|---|---|---|---|---|---|---|
| Run | Kind | Amount (g) | Kind | Amount (g) | Kind | Amount (g) | Bending Strength (Kg/mm²) | Modulus of Elasticity in Bending (Kg/mm²) | Elongation (%) | Bending Strength (Kg/mm²) | Modulus of Elasticity in Bending (Kg/mm²) | Elongation (%) |
| Ex. 10 | B-8 | 30 | H-1 | 30 | — | — | 22 | 562 | 8.8 | 219 | $13.2 \times 10^3$ | 1. |
| Ex. 11 | B-8 | 30 | H-2 | 5 | HA-1 | 5 | 25 | 581 | 9.3 | 235 | $13.5 \times 10^3$ | 1.8 |
| Ex. 12 | B-8 | 30 | " | 10 | " | 5 | 22 | 568 | 8.6 | 221 | $13.1 \times 10^3$ | 1.6 |
| Ex. 13 | B-8 | 30 | " | 5 | " | 20 | 21 | 565 | 8.7 | 225 | $13.3 \times 10^3$ | 1. |
| Ex. 14 | B-9 | 30 | " | 5 | HA-2 | 5 | 23 | 560 | 8.7 | 216 | $13.2 \times 10^3$ | 1.6 |
| Comp. Ex. 4 | — | — | " | 5 | HA-1 | 5 | 13 | 291 | 7.6 | 184 | $12.4 \times 10^3$ | 1.3 |
| Comp. Ex. 5 | B-12 | 1 | " | 5 | HA-2 | 5 | 13 | 295 | 7.5 | 183 | $12.5 \times 10^3$ | 1.4 |
| Comp. Ex. 6 | B-12 | 160 | " | 5 | " | 5 | 8 | 215 | 12.3 | 175 | $12.3 \times 10^3$ | 1.4 |

EXAMPLES 15 TO 31

A mixture of piperidine (85 g) and allyl glycidyl ether (107 g) was reacted at 150° C. for 3 hours while stirring. After completion of reaction, formation of Compound B-10 was confirmed by NMR spectral analysis.

B-10

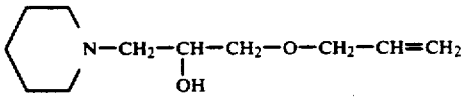

In analogous manners, starting compounds (V), (VI) or (VII), and (IV) were mixed in a weight ratio shown in Table 3 and the mixture was reacted to obtain Compound B-11 to B-22.

The procedures of Example 1 were repeated except that the additives shown in Table 3 and the hardeners and the hardening accelerators shown in Table 4 were used to prepare resin plates and carbon fiber composites. The mechanical properties of these samples were determined in the same manner as in Example 1. The results obtained are shown in Table 4 below.

TABLE 3

| | Starting Compounds | | | |
|---|---|---|---|---|
| Additive | (V) or (VI) or (VII) | Amount (g) | (IV) | Amount (g) |
| B-11 | Dibenzylamine | 197 | Dipentene Monoxide | 152 |
| B-12 | Piperidine | 85 | Butyl Glycidyl Ether | 131 |
| B-13 | p-Aminobenzoic Acid | 137 | Limonene Dioxide | 168 |
| B-14 | N-Methyl-formamide | 59 | Ethylene Glycol Diglycidyl Ether | 175 |

| Additive | Chemical Structure |
|---|---|
| B-11 | 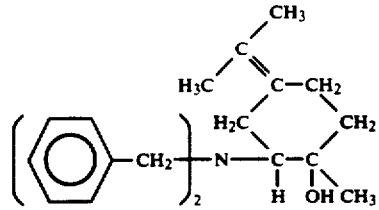 |
| B-12 | 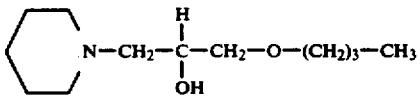 |
| B-13 | 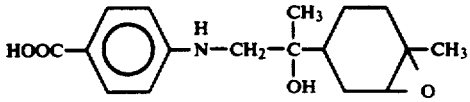 |
| B-14 | 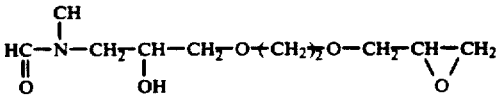 |

TABLE 3-continued

B-15

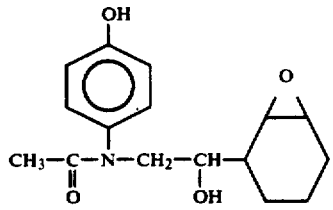

B-16

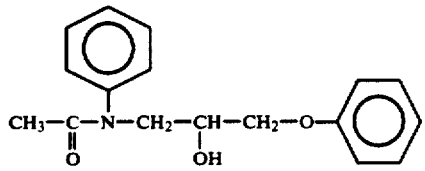

B-17

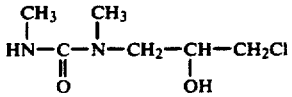

B-18

TABLE 3-continued

B-20

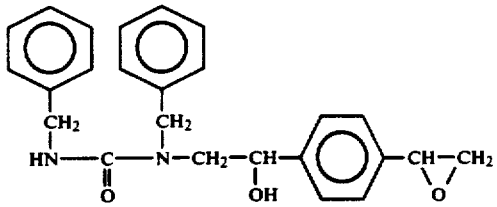

B-21

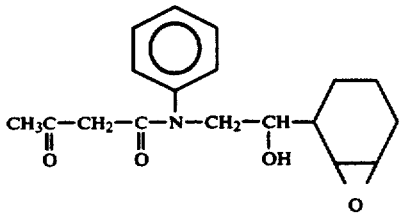

B-22

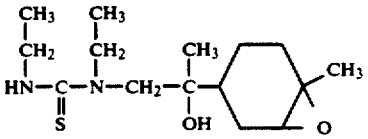

TABLE 4

| Run | Additive Kind | Additive Amount (g) | Hardener Kind | Hardener Amount (g) | Hardening Accelerator Kind | Hardening Accelerator Amount (g) | Properties of Resin Plate: Bending Strength (Kg/mm²) | Properties of Resin Plate: Modulus of Elasticity in Bending (Kg/mm²) | Properties of Resin Plate: Elongation (%) | Properties of Composite: Bending Strength (Kg/mm²) | Properties of Composite: Modulus of Elasticity in Bending (Kg/mm²) | Properties of Composite: Elongation (%) |
|---|---|---|---|---|---|---|---|---|---|---|---|---|
| Ex. 15 | B-11 | 30 | H-2 | 3 | HA-3 | 5 | 26 | 591 | 9.3 | 219 | $13.8 \times 10^3$ | 1.8 |
| Ex. 16 | B-12 | 40 | " | 5 | HA-1 | 2 | 27 | 590 | 9.4 | 220 | $13.9 \times 10^3$ | 1.8 |
| Ex. 17 | " | 40 | " | 5 | " | 9 | 25 | 582 | 9.1 | 218 | $13.6 \times 10^3$ | 1.9 |
| Ex. 18 | B-13 | 40 | " | 5 | HA-4 | 3 | 24 | 585 | 9.0 | 225 | $13.7 \times 10^3$ | 1.8 |
| Ex. 19 | " | 40 | " | 5 | " | 9 | 26 | 588 | 9.2 | 219 | $13.8 \times 10^3$ | 1.8 |
| Ex. 20 | B-14 | 30 | " | 5 | HA-1 | 3 | 25 | 584 | 9.3 | 227 | $13.8 \times 10^3$ | 1.7 |
| Ex. 21 | B-15 | 30 | " | 3 | HA-3 | 5 | 27 | 593 | 9.6 | 225 | $13.9 \times 10^3$ | 1.8 |
| Ex. 22 | B-7 | 40 | " | 5 | HA-1 | 2 | 28 | 592 | 9.4 | 225 | $14.0 \times 10^3$ | 1.9 |
| Ex. 23 | " | " | " | " | " | 9 | 25 | 583 | 9.0 | 216 | $13.5 \times 10^3$ | 1.9 |
| Ex. 24 | B-16 | 40 | " | 5 | HA-4 | 3 | 25 | 586 | 9.0 | 226 | $13.8 \times 10^3$ | 1.8 |
| Ex. 25 | " | " | " | " | " | 9 | 27 | 590 | 9.3 | 226 | $13.9 \times 10^3$ | 1.9 |
| Ex. 26 | B-17 | 30 | H-2 | 5 | HA-1 | 3 | 24 | 581 | 9.1 | 223 | $13.5 \times 10^3$ | 1.8 |
| Ex. 27 | B-18 | 30 | H-2 | 3 | HA-3 | 5 | 26 | 590 | 9.4 | 224 | $14.0 \times 10^3$ | 1.9 |
| Ex. 28 | B-19 | 40 | H-2 | 5 | HA-1 | 2 | 25 | 588 | 9.4 | 219 | $13.9 \times 10^3$ | 1.9 |
| Ex. 29 | " | " | " | " | HA-1 | 9 | 26 | 585 | 9.3 | 230 | $13.5 \times 10^3$ | 1.9 |
| Ex. 30 | B-20 | 40 | " | " | HA-4 | 3 | 24 | 590 | 9.0 | 226 | $13.8 \times 10^3$ | 1.7 |
| Ex. 31 | " | " | " | " | " | 9 | 28 | 591 | 9.3 | 219 | $13.8 \times 10^3$ | 1.8 |

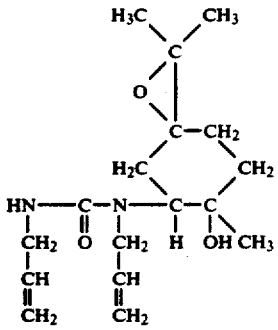

B-19

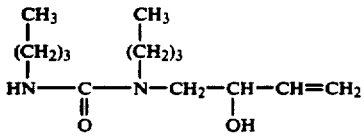

While the invention has been described in detail and with reference to specific embodiments thereof, it will be apparent to those skilled in the art that various changes and modifications can be made therein without departing from the spirit and scope thereof.

What is claimed is:

1. An intermediate for a composite material, which intermediate comprises carbon fibers impregnated with an epoxy resin composition containing epoxy resin and at least one of compounds represented by formula (I):

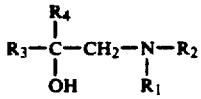

(I)

wherein $R_1$ and $R_2$, which may be the same or different, each represents *a hydrogen atom or* a substituted or unsubstituted, saturated alicyclic group having 5 to 17 carbon atoms, a substituted or unsubstituted aromatic group having 6 to 17 carbon atoms, or a substituted or unsubstituted, saturated or unsaturated 5- or 6-membered heterocyclic group containing N, O or S as hetero atoms or a group of formula

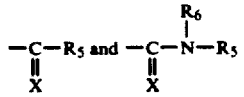

wherein $R_5$ and $R_6$, which may be the same or different, each represents a hydrogen atom or a substituted or unsubstituted, saturated aliphatic group having 1 to 17 carbon atoms, a substituted or unsubstituted, saturated alicyclic group having 5 to 17 carbon atoms, an aromatic group having 6 to 17 carbon atoms, or a substituted or unsubstituted, saturated 5- or 6-membered heterocyclic group containing N, O or S as hetero atoms, *provided that not more than one of $R_1$ and $R_2$ are hydrogen, and provided that $R_1$ and $R_2$ may combine to form an aromatic ring;*

$R_3$ and $R_4$, which may be the same or different, each has the same meaning as defined for $R_1$ and $R_2$, or a group of the formula R—$OCH_2$— wherein R has the same meaning as defined for $R_1$ and $R_2$ *except that R is not a hydrogen atom*; and X represents an oxygen atom, a sulfur atom or N-$R_7$ wherein $R_7$ [represents a hydrogen atom or] has the same meaning as defined for $R_1$ and $R_2$.

2. An intermediate as in claim 1, wherein the substituent for the substituted aliphatic, alicyclic, aromatic or heterocyclic group as represented by $R_1$, $R_2$, $R_5$, $R_6$ or $R_7$ is a halogen atom, an alkoxy group having 1 to 3 carbon atoms, an aryloxy group having 6 to 17 carbon atoms or an acyl group having 2 to 7 carbon atoms.

3. An intermediate as in claim 1, wherein $R_2$ contains a substituted or unsubstituted aromatic group.

4. An intermediate as in claim 1, wherein at least one of $R_3$ and $R_4$ contains a substituted or unsubstituted, saturated alicyclic or aromatic group.

5. An intermediate as in claim 1, wherein the compound or compounds is or are present in an amount of from 2 to 150 parts by weight per 100 parts by weight of the total amounts of the epoxy resin composition.

6. An intermediate as in claim 5, wherein the compound or compounds is or are present in an amount of from 10 to 50 parts by weight per 100 parts by weight of the total amounts of the epoxy resin composition.

7. An intermediate as in claim 1, wherein the resin composition further contains a hardener, a hardening accelerator, or both.

8. An intermediate as in claim 7, wherein the hardener is present in an amount of from 40 to 90% of the chemical equivalent amounts based on the total epoxy functional group.

9. An intermediate as in claim 8, wherein the hardener is present in an amount of from 50 to 80% of the chemical equivalent amounts based on the total epoxy functional group.

10. An intermediate as in claim 7, wherein the hardener is dicyandiamide.

11. An intermediate as in claim 7, wherein the hardener accelerator is present in an amount of from 1.5 to 15 parts by weight per 100 parts by weight of the total amounts of the epoxy resin and the additives.

12. An intermediate as in claim 11, wherein the hardening accelerator is present in an amount of from 2 to 10 parts by weight per 100 parts by weight of the total amounts of the epoxy resin and the additives.

13. An intermediate as in claim 7, wherein the hardening accelerator is a compound represented by [the] formula [(I)] *(II)*:

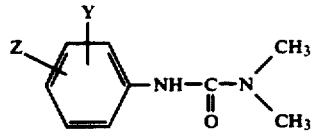

(II)

wherein Y and Z, which may be the same or different, each represents a hydrogen atom, a chlorine atom, a bromine atom, a nitro group, a methyl group, a methoxy group or an ethoxy group.

14. An intermediate as in claim 1, wherein the epoxy resin composition comprises at least one preliminary condensate which is obtained by subjecting at least one polyamine or acidic substance having a polycarboxylic group, a polycarboxylic acid anhydride group or a mixed group thereof and an epoxy resin having at least one epoxy group at a chemical equivalent ratio of from 1:1 to 1:6 to heat treatment at a temperature of from 50° to 200° C. to increase the viscosity of the mixture at least 3 times without inducing gelatin.

15. An intermediate as in claim 14, wherein the chemical equivalent ratio is from 1:1.4 to 1:6.

16. An intermediate as in claim 15, wherein the chemical equivalent ratio is from 1:1.5 to 1:5.

17. An intermediate as in claim 14, wherein the epoxy resin is bisphenol A diglycidyl ether.

18. An intermediate as in claim 14, wherein the polyamine is 4,4'-diaminodiphenylsulfone.

19. An intermediate for a composite material, which intermediate comprises a carbon fiber impregnated with an epoxy resin composition containing at least one compound represented by [the] formula (I):

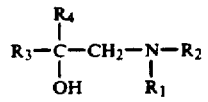

(I)

wherein $R_1$ and $R_2$, *which may be the same or different*, each represents a substituted or unsubstituted, saturated alicyclic group having 5 to 17 carbon atoms, a substituted or unsubstituted aromatic group having 6 to 17 carbon atoms, or a substituted or unsubstituted, saturated or unsaturated 5- or 6-membered heterocyclic group containing N, O or S as hetero atoms *or a group of formula*

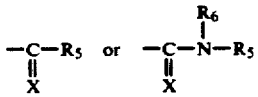

*wherein $R_5$ and $R_6$, which may be the same or different, each represents a hydrogen atom or a substituted or unsubstituted saturated aliphatic group having 1 to 17 carbon atoms, a substituted or unsubstituted, saturated alicyclic group having 5 to 17 carbon atoms, an aromatic group*

*having 6 to 17 carbon atoms, or a substituted or unsubstituted, saturated 5- or 6-membered heterocyclic group containing N, O or S as hetero atoms, provided that $R_1$ and $R_2$ may combine to form an aromatic ring;*

$R_3$ and $R_4$, which may be the same or different, each has the same meaning as defined for $R_1$ and $R_2$, or a group of the formula $R—OCH_2—$ wherein R has the same meaning as defined for $R_1$ and $R_2$; and X represents an oxygen atom, a sulfur atom or [$N—R_6$] $N—R_7$ wherein [$R_6$ represents a hydrogen atom or] $R_7$ has the same meaning as defined for $R_1$ and $R_2$, $R_1$, $R_2$, $R_3$ and $R_4$ thus represent a bulky and highly rigid substituent.

* * * * *